United States Patent [19]

Schucart et al.

[11] Patent Number: 5,643,228

[45] Date of Patent: Jul. 1, 1997

[54] CATHETER

[75] Inventors: David E. Schucart, Homewood; Edward M. Goldberg, Glencoe; Lev A. Melinyshyn, Buffalo Grove, all of Ill.

[73] Assignee: Uresil Corporation, Skokie, Ill.

[21] Appl. No.: 557,716

[22] Filed: Nov. 13, 1995

[51] Int. Cl.[6] .................................................. A61M 25/00
[52] U.S. Cl. ........................................... 604/264; 604/280
[58] Field of Search ................................ 604/264, 280, 604/281, 48, 50–53, 272, 273, 274

[56] References Cited

U.S. PATENT DOCUMENTS

| | | | |
|---|---|---|---|
| 4,784,638 | 11/1988 | Ghajar et al. | 604/264 X |
| 4,846,814 | 7/1989 | Ruiz | 604/281 |
| 4,968,306 | 11/1990 | Huss et al. | 604/264 |
| 4,968,307 | 11/1990 | Dake et al. | 604/264 |
| 5,242,395 | 9/1993 | Maglinte | 604/264 X |
| 5,250,034 | 10/1993 | Appling et al. | |
| 5,267,979 | 12/1993 | Appling et al. | |
| 5,399,158 | 3/1995 | Lauer et al. | |
| 5,425,723 | 6/1995 | Wang | 604/280 |

OTHER PUBLICATIONS

"Coaxial System Improves Thrombolysis of Ischemia," Thomas McNamara, MD., and Kelly Gardner, M.D., *Diagnostic Imaging*, Nov. 1991.

"100 Years of Progress," RSNA, 1994.

Instructions for Use, Mewissen™ Infusion Catheter System, Rev. Jun. 1994

"Pulse–Spray Pharmacomechanical Thrombolysis," Joseph J. Bookstein and Karim Valji, *Cardiovascular and Interventional Radiology*, 1992.

"Successful Thrombolysis of a Chronically Occluded Femoropopliteal Synthetic Bypass Graft via the Popliteal Appraoch: Case Report," Patrick Hall Sriram S. Iyer and Gerald Dorros, *Cardiovascular and Interventional Radiology*, 1991.

"Over–the–Wire Thrombolysis Using the Mewissen Infusion™ Catheter," Mark W. Mewissen, M.D., Department of Radiology Medical College of Wisconsin, Milwaukee, Wisconsin.

Instructions for Use, Pulsed Infusion System, Apr. 1991.

"Symptomatic Native Arterial Occlusions: Early Experience with Over–the–Wire Thrombolysis," Mark W. Mewissen, MD., Paul L. Minor, MD., Gary A. Beyer, MD., Elliot O. Lipchik, M.D. *Cardiovascular and Interventional Radiology*, 1990.

"Pharmacomechanical Thrombolysis and Angioplasty in the Management of Clotted Hemodialysis Grafts: Early and Late Clinical Results," Karim Valiji, MD., Joseph J. Bookstein, MD., Anne C. Roberts, MD., Gary B. Davis, MD., *Cardiovascular and Interventional Radiology*, 1991.

*Primary Examiner*—John D. Yasko
*Attorney, Agent, or Firm*—Laff, Whitesel, Conte & Saret, Ltd.

[57] ABSTRACT

A catheter for introducing fluid into the vascular system includes ports in the catheter's sidewall which are obliquely angled with respect to the longitudinal axis of the catheter. Certain pairs of ports are oriented toward each other, and certain other pairs of ports are oriented away from each other. The arrangement of ports causes fluid to exit the ports in streams which are oriented at oblique angles corresponding to the angles of the port. The obliquely angled streams create advantageous circulation paths proximate to the catheter which generally improve efficacy of the injected fluid associated with the medical application. The catheter may be used for a variety of purposes, including to perform thrombolysis.

18 Claims, 2 Drawing Sheets

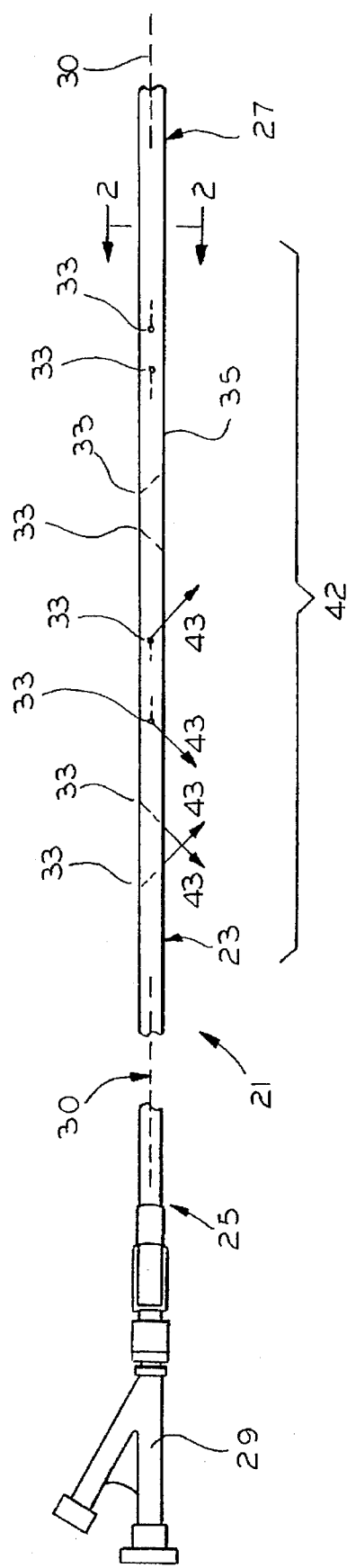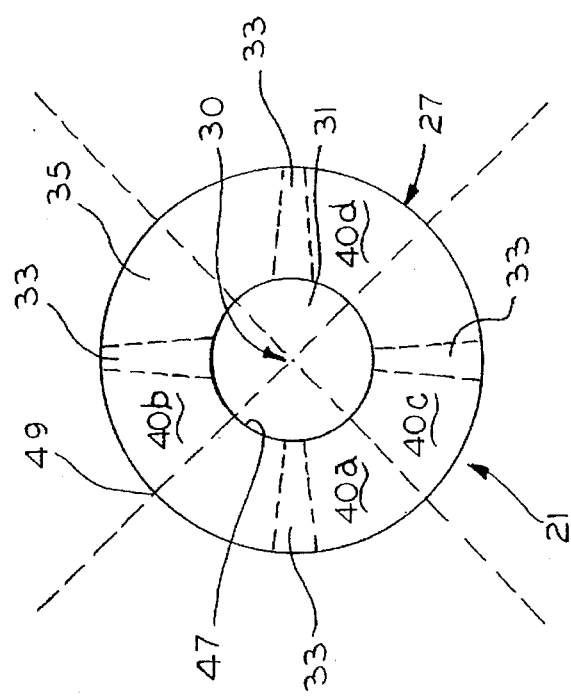

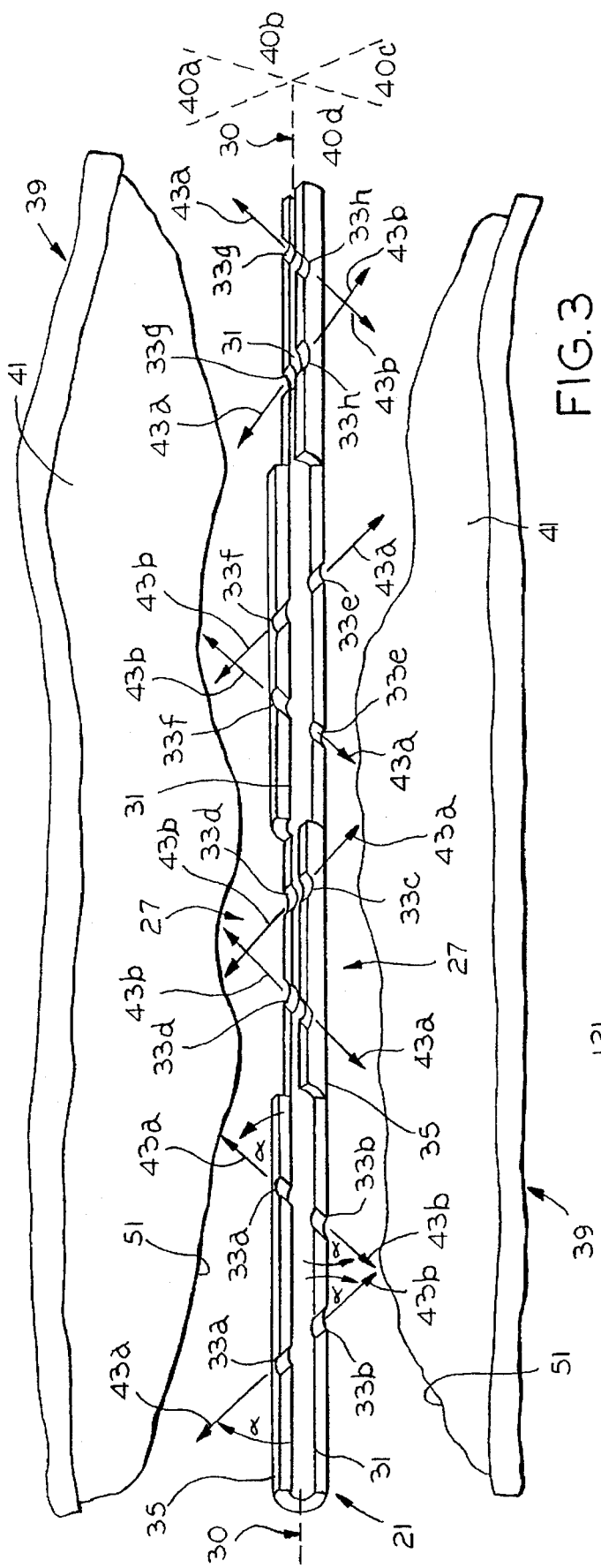
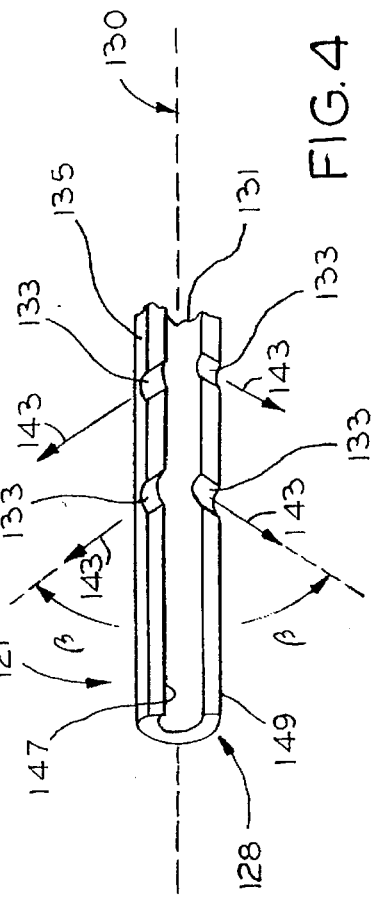
FIG. 3
FIG. 4

CATHETER

FIELD

The present invention relates to a catheter for use in the vascular system, and, more particularly, to a catheter having ports in its sidewall.

BACKGROUND

Catheters for delivery of material, generally fluids, into anatomical systems such as the vascular system are known in the art. Such catheters generally include an elongated catheter body with a sidewall which defines a catheter lumen. The catheter lumen has one end, referred to as the proximal end, through which fluid is introduced into the catheter lumen and another end, referred to as the distal end, from which fluid exits from the catheter lumen. One catheter design uses a single catheter lumen which is inserted into the anatomical system with the aid of a guidewire which passes through the lumen.

Fluid introduced into the proximal end of the catheter is generally passed through the lumen of the catheter under pressure supplied at or near the proximal end. The fluid then leaves the catheter through ports generally disposed at or near the distal end of the catheter. Such ports may include a hole at the end of the distal portion of the catheter. Various designs known in the art include one or more holes through the sidewall of the catheter, such as catheters by Mewissen (Meditech), EDM (Referral Systems Group), and the various MacNamara catheter systems, all of which are referenced in *Diagnostic Imaging*, Nov. 1, 1991. A catheter referred to in "Pulse-Spray Pharmacomechanical Thrombolysis," J. J. Bookstein and K. Valji, *Cardiovascular and Interventional Radiology*, v. 14, pp. 352–54 ("Bookstein"), has exit slits spaced along its distal end to perform pulse-spray pharmacomechanical thrombolysis. Bookstein emphasizes use of high-pressure pulses of brief duration to optimize thrombolysis procedures using urokinase as the fibrinolytic agent. Bookstein further describes using pulse-sprays from sidewall slits to perform angiography, and to perform thrombolysis on dialysis grafts.

U.S. Pat. Nos. 5,250,034 and 5,267,979 to Appling et al disclose side-slit catheters wherein the slits are configured to serve as pressure responsive valves, thereby resisting back flow of fluid into the catheter through the slits.

Although these two patent references, as well as the other above cited references, disclose various patterns and configurations of apertures in the sidewalls of catheters, in all of these references the fluid exits the catheter lumen generally orthogonally with respect to the longitudinal axis of the catheter lumen. For this and for various other reasons, current catheters suffer from various disadvantages and drawbacks when used to introduce fluids into anatomical systems, such as the vascular system. For example, when used to perform thrombolysis, fluid must be introduced at or near the thrombus to minimize the risk of clot fragmentation that can result in distal embolization occurring prior to effective clearing of the initial occlusion. Such clot fragmentation may result in tandem lesions, which may further restrict blood supply to the affected body part of the patient or cause other undesirable complications. The prior art has attempted to address these risks by increasing the pressure or exit force of the fluid from the side holes of the catheter, by increasing the number or varying the size of the side holes in the catheter, or both.

In addition, because of the invasive nature of using catheters to introduce fluid into the vascular system, such as in performing thrombolysis of a blood vessel, it is desirable to shorten the time needed to effectively introduce the desired fluid. In particular, the amount of time required to lyse a thrombus is preferably kept to a minimum. To minimize the time needed for lysing a thrombus or for performing any other procedure involving introduction of fluid through a catheter, it is necessary for the fluid to be accurately and efficiently introduced at the desired location in the vascular system. In the context of thrombolysis, for example, the lytic agent needs to be dispersed within the blood vessel in such a way that it acts to effectively dissolve the clot in a minimum amount of time. The catheters and associated procedures of the prior art need to be improved to more optimally place and disperse fluid, such as lyric agents, in the zone of interest within the patient's vascular system.

Thus, there is a need for an improved catheter which introduces fluid into the vascular system in a manner which increases the efficacy of the fluid being introduced, thereby minimizing both the amount of fluid needed to perform the desired procedure, as well as the time required for effectively completing such procedure.

SUMMARY

Accordingly, an object of this invention is to provide a new and improved catheter which optimally disperses fluid into the vascular system.

Further, it is an object of this invention when used in performing thrombolysis to increase the reaction of the lyric agent with the thrombus and thereby manipulate the thrombus.

According to the present invention, the foregoing and other objects and advantages are attained by an apparatus with one or more ports extending through the sidewall of a catheter. The ports extend through the sidewall at an oblique angle relative to the longitudinal axis of the catheter, thereby introducing the fluid into the vascular system in one or more obliquely angled streams.

According to another aspect of the invention, at least two ports are spaced from each other along the catheter sidewall, the ports oriented at oblique angles relative to the longitudinal axis of the catheter lumen. The oblique angles are selected so that the fluid stream from one of the ports exits toward the fluid stream exiting the other port. This arrangement has been found to lyse or disrupt the thrombus most effectively. Another suitable arrangement of ports according to the present invention would be to orient a pair of ports to face away from each other, thereby directing the stream of fluid from one port away from the stream of fluid of the other port.

In accordance with still another aspect of the present invention, four ports are formed in a sidewall of the apparatus by passing a laser beam at an oblique angle relative to the longitudinal axis through the catheter lumen at two locations and through two points on the circumference of the sidewall. The laser beam is oriented so that two of the four ports are spaced from each other along one side of the sidewall and face each other, and the other two of the four ports are spaced from each other along the opposite side of the sidewall and are oriented to face away from each other.

Still other embodiments of the present invention would include multiple groups of the four ports described above spaced longitudinally along an elongated catheter body. Each group of four ports may be oriented differently from the adjacent group of four ports. The ports may comprise holes having substantially circular cross sections of between 0.001" to 0.012" in diameter, and, preferably, between 0.005" and 0.010", and the oblique angle of the ports may be between 30° and 60° to the longitudinal axis of the catheter and, preferably, the oblique angle of the ports is about 45°.

Another aspect of the present invention is a method for reducing a clot in a blood vessel which involves injecting a lytic agent through a catheter and into the blood vessel substantially at the location of the clot, the lytic agent being injected in a stream at an oblique angle with respect to the longitudinal axis of the catheter. Another method in accordance with the present invention involves introducing fluid into the vascular system by emitting multiple streams, at least one of the streams angled toward another of the streams.

Still other objects, advantages, and novel aspects of the present invention will become apparent in the detailed description of the invention that follows, in which the preferred embodiment of the invention is shown by way of illustration of the best mode contemplating for carrying out the invention, and by reference to the attached drawings in which:

BRIEF DESCRIPTION OF THE DRAWINGS

FIG. 1 is a side elevational view of an apparatus according to the present invention showing streams of fluid exiting at an oblique angle relative to the longitudinal axis;

FIG. 2 is an enlarged, cross-sectional view taken along line 2—2 of FIG. 1;

FIG. 3 is an enlarged, sectional perspective view of a portion of the apparatus of FIG. 1 shown within a blood vessel; and FIG. 4 is a cross-sectional side view of an alternative embodiment of the present invention.

DESCRIPTION

Referring now to the drawings, and more particularly to FIGS. 1–3, a catheter 21 illustrates one embodiment of the present invention. The catheter 21 is sized and configured to introduce fluid into the vascular system through ports 33 which are obliquely angled with respect to longitudinal axis 30 of the catheter 21. The fluid exits from the ports 33 in streams 43 indicated by directional arrows. When they exit the ports 33, the streams 43 have the same oblique orientation as the ports 33.

The catheter 21 has an elongated catheter body 23 with a proximal portion 25 at one end and a distal portion 27 at the other end which is adapted to be inserted into the vascular system. The catheter body 23 has a sidewall 35 which defines a lumen 31 (FIGS. 2 and 3). The lumen 31 extends substantially along the length of the catheter body 23. The catheter 21 includes means, here shown as a Touhy-Borst Y adaptor 29, for introducing fluid into the lumen 31 at or near the proximal portion 25. The Touhy-Borst Y adaptor 29 also allows pressure to be applied to the fluid introduced into the lumen 31 so that the fluid is expelled from the lumen through the obliquely angled ports 33.

One intended use of the catheter 21 is to inject or otherwise deliver lytic agents or enzymes such as urokinase into blood vessels to lyse clots. A portion of the catheter 21 is shown in FIG. 3 after having been inserted into a blood vessel 39 at or near a clot 41 which is to be lysed. When pressure is exerted on the fluid within the lumen 31, the fluid is expelled from the ports 33 in the streams 43 as discussed above. As shown in FIG. 3, the obliquely angled ports 33 direct the streams of fluid 43 (shown as directional arrows) at an oblique angle $\alpha$ with respect to the longitudinal axis 30, which oblique angle $\alpha$ corresponds to the oblique angle at which the ports 33 are oriented.

The placement of the ports 33 in relation to each other and the value of the angle $\alpha$ are selected so as to generally create advantageous localized circulation of the injected fluid and other bodily fluids proximate to the ports 33. In this particular embodiment, the ports 33 include multiple port pairs 33a–h which are disposed along the length of the sidewall 35 and at different selected points about the circumference of the sidewall 35. Ports 33a are located on one side of the sidewall 35 and ports 33b are located on the opposite side of the sidewall 35, that is, at a point on the circumference of the sidewall 35 which is oriented approximately 180° from the side on which ports 33a have been disposed.

The ports 33a comprise a pair of ports oriented to face away from each other and the ports 33a thus direct the flow at fluid from one of the ports 33a away from the flow of fluid at the other of the ports 33a. The ports 33b comprise a pair of ports spaced from each other along the sidewall and oriented to face toward each other. Each of the ports 33a and 33b are angled at the oblique angle indicated by $\alpha$ with respect to the longitudinal axis 30, which in this particular embodiment ranges between about 30° and 60° and is preferably approximately 45°.

Fluid exiting from the ports 33a and 33b is directed into streams 43a and 43b, respectively, which flow in the directions generally indicated by the arrows. As discussed previously with reference to FIG. 1, the streams of fluid 43a and 43b shown in FIG. 3 are oriented at oblique angles with respect to the longitudinal axis 30 corresponding to the oblique angles of the ports 33a and 33b. This oblique orientation of the streams 43a and 43b has been found to improve lysing of a thrombus when the catheter is used to perform thrombolysis. The improvement is believed to arise from eddies in the injected fluid and the adjacent vascular fluid caused by the obliquely angled streams. Some of these eddies are likely to be turbulent. The forces associated with these eddies resemble an agitator-type action and assist in the dispersion of the fluid, as well as improving the ability of the fluid to penetrate the surface 51 of the clot 41. In some applications, the streams 43b, which face each other, may intermix with each other either directly or after rebounding off the walls of the blood vessel. Such intermixing also improves the efficacy of the injected fluid. The streams 43a emanating from the ports 33a draw fluid from the area between them and also generally create a region of circulation between them which may contain eddies or otherwise become turbulent, again aiding the dispersion of the lytic agent within the clot 41.

The two port pairs 33c and 33d are oriented with respect to each other in a manner similar to the two port pairs 33a and 33b, respectively, except that the port pairs 33c and 33d have an orientation rotated about 90° along the circumference of the sidewall 35 in relation to the port pairs 33a and 33b. Similarly, the group of four ports 33e and 33f have been rotated about 90° from the orientation of the adjacent port pairs 33c and 33d; and, the port pairs 33g and 33h have been rotated about 90° from the orientation of the two port pairs 33e and 33f.

The above described arrangement of the ports 33a–h creates multiple groups of four ports spaced longitudinally along the catheter body 23. Also by virtue of this arrangement, one pair of ports faces away from each other and one pair of ports faces toward each other in each of the four quadrants 40a–d (FIGS. 2 and 3) of the cross-section of the catheter 21.

With regard to the pairs of ports 33b, 33d, 33f, 33h, each port is oriented toward another corresponding port and the corresponding streams of fluid are sent toward each other in the direction 43b. The other port pairs 33a, 33c, 33e and 33g have ports facing away from each other and thus eject fluid in streams 43a away from each other. The advantageous circulatory pattern described previously with reference to ports 33a and 33b is thus present at multiple locations about the circumference of the sidewall 35, resulting in advantageous flow patterns emanating from all four quadrants 40a–d of the sidewall 35.

A suitable way of creating the ports 33a–33h is to cut obliquely through the longitudinal axis of the catheter body 23 using a carbon dioxide laser. The laser beam is oriented to intersect the body of the catheter at an oblique angle and extend through the lumen and thereby form two ports at two points on the circumference of the catheter body in a single manufacturing operation. Referring particularly to FIG. 3, then, a laser is directed obliquely at an angle α to form one of the ports 33a and a corresponding one of the ports 33b which is closest to the port 33a. In other words, the port 33a and the port 33b are generally both aligned at an oblique angle with each other corresponding to the orientation of the oblique cut made by the $CO_2$ laser. The remaining ports 33 as shown in FIG. 3 are similarly cut through opposing points on the circumference of the catheter body 23.

The laser beam is oriented to pass through two points on the circumference of the catheter body 23 and through the lumen 31. The beam intersects a plane passing through the longitudinal axis 30 at an oblique angle, in this embodiment having a value of α. Each port 33 thus has a corresponding port 33 at an opposing point on the circumference of the catheter body 23, and the two ports orient fluid emanating from them in two, oblique directions which are about 180 degrees from each other. In particular, each of the ports 33a ejects fluid in the opposite direction of a corresponding one of the ports 33b. The ports 33c and 33d, 33e and 33f, and 33g and 33h form similar pairs of oppositely oriented ports.

This oblique, opposite orientation, in turn, means that the vector for the fluid flowing out of one of the oppositely-oriented ports includes a vector component parallel to the longitudinal axis 30 and toward one end of the catheter, while the vector for the fluid flowing out of the other, corresponding port on the opposite side has a vector component parallel to the longitudinal axis 30 but toward the opposite end of the catheter. These oppositely oriented vector flow components are at opposing points on the circumference of the catheter 23 and at the same general location along the length of the catheter body 23. These flow components may thus create additional circulation paths between the opposing points on the circumference of the catheter in many applications.

One possible use of the catheter 21 is to perform thrombolysis as described below with particular reference to FIG. 3. The sidewall 35 of the catheter 21 is at least partially received within the blood vessel 39. The distal portion 27 of the catheter is positioned in operative proximity to the clot 41, that is, at a location relative to the clot 41 which is known by those skilled in the art to have a likelihood of dissolving the clot 41 when a lytic agent exits the distal portion 27. A lytic agent or enzyme in fluid form is introduced into the lumen 31 from any suitable reservoir (not shown) and, optionally, through the Touhy-Borst adaptor 29 (FIG. 1). The lytic agent is directed through the lumen 31 and out of the ports 33 in multiple streams 43 which are oriented obliquely as indicated by the directional arrows. The ports 33 are spaced along the catheter sidewall 35 and thus form multiple points of emanation for fluid exiting the lumen 31 from the ports 33.

Since the ports 33 are obliquely angled with respect to the longitudinal axis 30 of the catheter, the streams 43b are oriented toward each other and the streams 43a are oriented away from each other and generally draw fluid outward from between them. The fluid flows caused by the streams 43 increase eddies and turbulence to create a flow pattern similar to that created by a washing machine agitator, which has been found to improve lysing of the clot 41.

In addition, since the streams are obliquely angled, one component of their flow is parallel to the longitudinal axis 30 of the catheter. Thus, localized circulation parallel to the longitudinal axis 30 is created, which may also improve lysing of the clot 41. When the fluid strikes the clot at an oblique angle, the fluid may also rebound from the blood vessel or clot at a corresponding rebound angle. This rebounding of the streams at oblique angles is likely to complicate the circulation pattern, creating still more eddies and turbulence which also contribute to more effective dispersion of the lyric agent and thereby increase the lysing rate. The arrangement of ports 33a–h in this embodiment also causes the streams 43 to exit from opposite points on the circumference of the catheter body 23 and in opposite, obliquely angled directions. This further enhances the flow pattern by creating circulation paths between the opposing points on the circumference of the catheter 21.

FIG. 4 illustrates an alternative embodiment of the present invention in which a catheter has ports 133 on sidewall 135 of catheter lumen 131. The ports 133 are oriented to direct fluid at an oblique angle β with respect to longitudinal axis 130. Streams of fluid 143 generally follow the directions indicated by the arrows, which directions are toward distal tip 128 of the catheter. Fluid ejected from the lumen 131 thus flows generally toward the distal tip 128 and generally creates localized circulation of the injected fluid and any other fluids present at the area of injection.

Although FIG. 4 shows only 4 of the ports 133 generally oriented toward the distal tip 128, additional ports may be provided at additional locations along the sidewall 135 and oriented in the same direction and at the same angle as the ports 133, or alternately, at different angles and in different directions.

Further alternative embodiments may, of course, further vary the number, spacing, or arrangement of the obliquely angled ports to produce advantageous flow patterns and eddies in operative proximity to the vascular region to be treated.

The ports 33, 133 have a substantially circular cross section with suitable diameters ranging from about 0.012" to as small as about 0.001", with a preferable diameter of about 0.005" to 0.010". Although a carbon dioxide laser may be used to cut the ports 33, 133 various alternative means are also suitable for creating the ports. For example, an excimer laser or a TEA laser have been found suitable for creating holes as small as 0.001" in diameter. Such smaller diameter ports may be preferable in certain medical applications, such as when a small volume of fluid is to be injected at a high pressure. The ports 33a–33h have been located along the sidewall 35 over a length of about 4", creating a corresponding infusion length 42.

Although the ports 33, 133 have substantially circular cross sections, alternative cross sections and alternative shapes for the ports may be used, so long as the shape and contour of the ports cause fluid to flow from the ports at an angle which is oblique relative to the longitudinal axis of the lumen.

In addition to varying the shapes of the ports, further alternative embodiments may include any number of obliquely angled ports spaced over the sidewall of the catheter in any number of patterns or arrangements. For those medical applications in which a relatively short infusion length is desirable, the ports are located along only a relatively short length of the sidewall; conversely, for those medical applications requiring a longer infusion length, the spacing of the ports occurs over a generally longer length of the sidewall. The number of ports, of course, may not only be varied depending on the desired infusion length, but may also be varied to suit the particular volume of fluid which needs to be injected for the particular application.

Suitable diameters for the catheter lumen 31 and the catheter body 23 have been found to be the same as those commercially available, and will vary depending on the particular application or anatomical system to receive the fluid. Similarly, the material used to create the catheter body may be selected from any of those currently used to make commercially available catheters. For example, a suitable wall thickness for a catheter according to the present invention has been found to range between about 0.008" and 0.014". Suitable materials for the sidewall include biocompatible thermoplastic materials such as nylon or polyurethane, with nylon presently being preferred.

In addition to the advantages of the present invention which are apparent from the above description, when the present invention is used to perform thrombolysis, the increased rate of lysing of the clot allows the procedure to be performed more quickly and with less injection of fluid. The discomfort of the patient is thus correspondingly reduced. Increased dispersion of the lytic agent improves dissolution of the clot and minimize the risk of undesireable fragmentation of the clot.

The improved dispersion of the fluid to be injected produces similar advantages when the invention is used in other medical applications, such as angiography, where quick and effective dispersal of fluids is desired.

While the present invention has been described with reference to preferred embodiments thereof, illustrated in the accompanying drawings, various changes and modifications can be made by those skilled in the art without departing from the spirit and scope of the present invention; therefore, the appended claims are to be construed to cover equivalent structures.

What is claimed is:

1. A catheter for introducing fluid into a blood vessel comprising:

an elongated catheter body having a sidewall defining a catheter lumen, the catheter body having a proximal portion with means for introducing fluid streams into the lumen and a distal portion adapted to be received into the vessel; and at least two ports extending through the sidewall at oblique angles relative to the longitudinal axis of the lumen, said ports being either oriented toward one another to send corresponding streams of fluid toward each other or oriented away from each other to send one stream of fluid toward one end of the catheter and the other stream toward the opposite end of the catheter.

2. An apparatus for introducing fluid into the vascular system comprising:

an elongated body having a proximal portion and a distal portion, the distal portion sized to be inserted into the vascular system, the body having a sidewall defining a lumen, means for introducing fluid streams into the lumen under pressure; and at least two ports extending through the sidewall at the distal portion, the ports having means for directing the fluid out of the lumen at oblique angles relative to the longitudinal axis of the lumen, said ports being either oriented toward one another to send corresponding streams of fluid toward each other or oriented away from each other to send one stream of fluid toward one end of the catheter and the other stream toward the opposite end of the catheter.

3. The apparatus of claim 2 comprising more than two ports spaced along the length of the sidewall.

4. The apparatus of claim 2, wherein at least two ports are oriented toward each other.

5. The apparatus of claim 2, wherein at least two ports are oriented away from each other.

6. The apparatus of claim 5, wherein one of the ports is located on one side of the elongated body and the other is located on the other side of the elongated body.

7. The apparatus of claim 5, wherein at least one pair of ports is located in each of the four quadrants of the circumference of the sidewall.

8. The apparatus of claim 2, wherein the ports comprise holes having a substantially circular cross-section with a diameter between about 0.001" and 0.012".

9. The apparatus of claim 2, wherein the ports comprise holes having a substantially circular-cross section with a diameter between about 0.005" and 0.010".

10. The apparatus of claim 2, wherein the oblique angles are between about 30 and 60 degrees with respect to the longitudinal axis of the lumen.

11. The apparatus of claim 1 comprising more than two ports spaced along the length of the sidewall.

12. The apparatus of claim 1, wherein the ports are oriented toward each other.

13. The apparatus of claim 1, wherein the ports are oriented away from each other.

14. The apparatus of claim 1, wherein at least one of the ports is located on one side of the elongated body and another is located on the other side of the elongated body.

15. The apparatus of claim 1, wherein at least one pair of ports is located in each of the four quadrants of the circumference of the sidewall.

16. The apparatus of claim 1, wherein the ports comprise holes having a substantially circular cross section with a diameter between about 0.001" and 0.012".

17. The apparatus of claim 1, wherein the ports comprise holes having a substantially circular-cross section with a diameter between about 0.005" and 0.010".

18. The apparatus of claim 1, wherein the oblique angles are between about 30 and 60 degrees with respect to the longitudinal axis of the lumen.

* * * * *